US007186824B2

(12) United States Patent
Aga et al.

(10) Patent No.: US 7,186,824 B2
(45) Date of Patent: Mar. 6, 2007

(54) REDUCTION INHIBITORY AGENT FOR ACTIVE-OXYGEN ELIMINATING ACTIVITY

(75) Inventors: Hajime Aga, Okayama (JP); Takashi Shibuya, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 488 days.

(21) Appl. No.: 10/670,525

(22) Filed: Sep. 26, 2003

(65) Prior Publication Data

US 2004/0058592 A1    Mar. 25, 2004

Related U.S. Application Data

(62) Division of application No. 09/034,336, filed on Mar. 4, 1998, now abandoned.

(30) Foreign Application Priority Data

Mar. 4, 1997   (JP) ................................. 9-063987
Jan. 14, 1998  (JP) ................................. 10-017647

(51) Int. Cl.
C07H 1/00         (2006.01)
(52) U.S. Cl. ................................................. 536/123.13
(58) Field of Classification Search ................. 514/53;
536/123.13
See application file for complete search history.

(56) References Cited

U.S. PATENT DOCUMENTS

| 4,806,343 | A |   | 2/1989  | Carpenter et al. |
| 4,839,164 | A |   | 6/1989  | Smith |
| 4,915,951 | A | * | 4/1990  | Baldeschwieler et al. ... 424/450 |
| 4,963,385 | A |   | 10/1990 | Antrim et al. |
| 5,059,518 | A |   | 10/1991 | Kortright et al. |
| 5,149,653 | A |   | 9/1992  | Roser |
| 5,169,767 | A |   | 12/1992 | Matsuura et al. |
| 5,242,792 | A | * | 9/1993  | Rudolph et al. ................ 435/2 |
| 5,472,863 | A |   | 12/1995 | Maruta et al. |
| 5,512,547 | A |   | 4/1996  | Johnson et al. |
| 5,518,742 | A |   | 5/1996  | Soeda et al. |
| 5,543,513 | A |   | 8/1996  | Mandai et al. |
| 5,556,771 | A |   | 9/1996  | Shen et al. |
| 5,567,424 | A |   | 10/1996 | Hastings |
| 5,578,469 | A | * | 11/1996 | Shibuya et al. .............. 435/100 |
| 5,747,300 | A | * | 5/1998  | Nishimoto et al. .......... 435/101 |
| 5,759,610 | A | * | 6/1998  | Nishimoto et al. .......... 426/658 |
| 5,827,886 | A |   | 10/1998 | Hersh et al. |
| 5,935,636 | A |   | 8/1999  | Nishimoto et al. |

FOREIGN PATENT DOCUMENTS

| CN | 1078117 A | 11/1993 |
| CN | 1079880 A | 12/1993 |
| CN | 1091262 A | 8/1994 |
| CN | 1094923 A | 11/1994 |
| CN | 1107297 A | 8/1995 |
| CN | 1107716 A | 9/1995 |
| DE | 3542309 A1 | 6/1987 |
| DE | 195 03 685 A | 8/1996 |
| EP | 0 297 887 A1 | 1/1989 |
| EP | 0297887 A1 * | 1/1989 |
| EP | 0 556 838 A1 | 8/1993 |
| EP | 0690 130 A1 | 6/1994 |
| EP | 0600730 A1 * | 6/1994 |
| EP | 0619951 A2 * | 10/1994 |
| EP | 0 628 630 A2 | 12/1994 |
| EP | 0 636 693 A2 | 2/1995 |
| EP | 0739986 A1 * | 4/1995 |
| EP | 0 691 344 A1 | 1/1996 |
| EP | 0 693 558 | 1/1996 |
| EP | 0 726 310 A | 8/1996 |
| EP | 0 739 986 A1 | 10/1996 |
| EP | 0 784 095 A2 | 7/1997 |
| EP | 0 816 509 A2 | 1/1998 |
| EP | 0868916 A2 | 10/1998 |
| EP | 0 933 428 A2 | 8/1999 |
| JP | 58-216695 A | 12/1983 |
| JP | 60 149972 A | 8/1985 |
| JP | 01-106829 A | 4/1989 |
| JP | 01-304882 A | 12/1989 |
| JP | 05-168435 A | 7/1993 |
| JP | 6 040845 A | 2/1994 |
| JP | 06-319503 A | 11/1994 |
| JP | 07-51063 A | 2/1995 |
| JP | 07-79739 A | 3/1995 |
| JP | 07-143876 A | 6/1995 |
| JP | 07-170977 A | 7/1995 |
| JP | 7 194378 A | 8/1995 |
| JP | 07-213283 A | 8/1995 |
| JP | 07-246097 A | 9/1995 |
| JP | 07-309770 A | 11/1995 |
| JP | 08-140595 A | 6/1996 |
| JP | 08-143466 A | 6/1996 |
| JP | 08-228736 A | 9/1996 |

(Continued)

OTHER PUBLICATIONS

[R] C. K. Lee, "Trehalose," Dev. Food Carbohydrates, 2(1), 1-89 (1980).*

(Continued)

Primary Examiner—L. E. Crane
(74) Attorney, Agent, or Firm—Browdy and Neimark, PLLC

(57) ABSTRACT

A reduction inhibitory agent for active-oxygen eliminating activity comprises trehalose as an effective ingredient. A method for inhibiting the reduction of active-oxygen eliminating activity comprises incorporating either trehalose or the reduction inhibitory agent into plant edible products and/or plant antioxidants. A composition is provided that reduces the active-oxygen eliminating activity of plant edible products and/or plant antioxidants.

2 Claims, No Drawings

FOREIGN PATENT DOCUMENTS

| | | | |
|---|---|---|---|
| JP | 09-56342 | A | 3/1997 |
| JP | 09-163943 | A | 6/1997 |
| JP | 09-275994 | A | 10/1997 |
| PL | 9400068-9 | A | 9/1995 |
| WO | WO 93/00807 | A1 | 1/1993 |
| WO | WO 95/01446 | A1 | 1/1995 |
| WO | WO 95/06126 | A1 | 3/1995 |
| WO | WO 96/00789 | A1 | 1/1996 |
| WO | WO 96/21030 | A1 | 7/1996 |
| WO | WO 97/17435 | A1 | 5/1997 |
| WO | WO 97/38095 | A1 | 10/1997 |
| WO | WO 97/42327 | A | 11/1997 |

OTHER PUBLICATIONS (S) N. Saito, "Characterization and Utilization of Trehalose (Japanese)," Brain Techno News, 70, 1-4 (Nov. 15, 1998).*

Imanari, Toshio et al., Igakuno Ayumi, vol. 101, pp. 496-497 (1977).

Carpenter et al., Modes of Stabilization of a Protein by Organic Solutes During Desication. Cryobiology, 25, pp. 459-470. (1988). No Month Given.

Argall, et al., "The Use of Trehalose-Stabilized Lyophilized Methanol Dehydrogenase from *Hyphomicrobium* X for the Detection of Methanol", Biochemistry and Molecular Biology International. Jul. 1993, vol. 30, No. 3, 491-497.

Carpenter, et al., "Modes of Stabilization of a Protein by Organic Solutes During Desiccation", Cryobiology. 1998, vol. 25, 459-470.

Carpenter, et al, "Separation of Freezing- and Drying-Induced Denaturation of Lyophilized Proteins Using Stress-Specific Stabilization", Archives of Biochemistry and Biophysics. Jun. 1993, vol. 303, No. 2, 456-464.

Carpenter, et al., "Stabilization of Phosphofructokinase during Air-Drying with Sugars and Sugar/Transition Metal Mixtures", Cryobiology. 1987, vol. 24, 455-464.

Carpenter, et al., "Stabilization of Phosphofructokinase with Sugars During Freeze-Drying: Characterization of Enhanced Protection in the Presence of Divalent Cations", Biochimica et Biophysica Acta. 1987, vol. 923, 109-115.

Goddijn, et al., "Inhibition of Trehalase Activity Enhances Trehalose Accumulation in Transgenic Plants", Plant Physiology. 1997, vol. 113, 181-190.

Hajime, et al., "Stabilization by Trehalose of Superoxide Dismutase-like Activity of Various Vegetables", Nippon Shokuhin Kagaku Kogaku Kaishi. 1998, vol. 45, 210-215, Biosis Abstr: PREV199800255288, only abstract supplied.

Lippert, et al., "Enzyme Stabilization by Ectoine-Type Compatible Solutes: Protection Against Heating, Freezing and Drying", Appl. Microbiol. Biotechnol. 1992, vol. 37, 61-65.

Ramos, et al., "Stabilization of Enzymes against Thermal Stress and Freeze-Drying by Mannosylglycerate", Applied and Environmental Microbiology. Oct. 1997, vol. 63, No. 10, 4020-4025.

Roser, et al., "A Sweeter Way to Fresher Food", New Scientist, IPC Magazines, May 15, 1993, vol. 138, 25-28.

Roser, Bruce, "Trehalose Drying: A Novel Replacement for Freeze-Drying", Biopharm., Sep. 1, 1991, vol. 4, No. 8, 47-53.

Roser, Bruce, "Trehalose, a New Approach to Premium Dried Foods", Trends in Food Science & Technology. Jul. 1991, 166-169.

Salek, et al., "Trehalose—Stabilisation of Osmophilicity and Viability of Baker's and Distiller's Yeast: Applications to Storage and Drying", Chem. Mikrobiol. Technol. Lebensm. 1995. vol. 17, No. 1/2, 14-21.

Sun, et al., "Cytoplasmic Vitrification and Survival of Anhydrobiotic Organisms", Comp. Biochem. Physiol. 1997, vol. 117A, No. 3, 327-333.

Uritani, et al, "Protection Effect of Disaccharides on Restriction Endonucleases During Drying under Vaccum", J Biochem, 1995, vol. 117, 774-779.

Aguilera J M et al "Preservation of biological materials under desiccation" Critical Reviews in Food Science and Nutrition vol. 37, No. 3 (1997) pp. 287-309.

Bhandal I S et al "Trehalose As Cryoprotectant for the Freeze Preservation of Carrot Daucus-Carota and Tobacco Cells" Plant Physiology, vol. 78, No. 2 (1985) pp. 430-432.

Colaco C et al "Extraordinary Stability of Enzymes dried in Trehalose: Simplified Molecular Biology" Bio/Technology, Nature Publishing Co. vol. 10, No. 9. (Sep. 1992) pp. 1007-1011.

Crowe J H et al "Interactions of sugars with membranes" Biochimica et Biophysica Acta vol. 947, No. 2 (Jun. 1988) pp. 367-384.

Crowe L M et al "Is trehalose special for preserving dry biomaterials?" Biophysical Journal, vol. 71, No. 4, (Oct. 1996) pp. 2087-2093.

Holmstrom K O et al "Drought Tolerance in Tobacco" Nature, Macmillan Journals LTD, vol. 379 (Feb. 1996) pp. 683-684.

Mouradian R et al "Degradation of Functional Integrity During Long-Term Storage of a Freeze-dried Biological Membrane" Cryobiology, vol. 22, No. 2 (1985) pp. 119-127.

Newman Y M et al "The Role of Trehalose and other Carbohydrates in Biopreservation" Biotechnology and Genetic Engineering Reviews, Intercept LTD. vol. 11 (Dec. 1993) pp. 263-294.

Panek A D "Trehalose metabolism: New horizons in technological applications" Brazilian Journal of Medical and Biological Research vol. 28, No. 2 (1995) pp. 169-181.

Rudolph A S et al "Dry Storage of Liposome-Encapsulated Hemoglobin a Blood Substitute" Cryobiology, vol. 27, No. 6 (1990) pp. 585-590.

Rudolph A S "The Freeze-Dried Preservation of Lipsome Encapsulated Hemoglobin A Potential Blood Substitute Cryobiology" vol. 25, No. 4 (1988) pp. 277-284.

Sola-Penna M et al "Protective role of trehalose in thermal denaturation of yeast pyrophosphatase" Zeitschrift fur Naturforschung, Journal of Biosciences (May 1994) vol. 49, No. 5-6 pp. 327-330.

C. K. Lee, "Trehalose," *Dev. Food Carbohydrates*, 2(1), 1-89 (1980).

N. Saito, "Characterization and Utilization of Trehalose (Japanese)," *Brain Techno News*, 70, 1-4 (1998).

* cited by examiner

US 7,186,824 B2

REDUCTION INHIBITORY AGENT FOR ACTIVE-OXYGEN ELIMINATING ACTIVITY

This is a divisional of Ser. No. 09/034,336, filed on Mar. 4, 1998, and now abandoned.

BACKGROUND OF THE INVENTION

1. Field of the Invention

The present invention relates to a reduction inhibitory agent for active-oxygen eliminating activity, uses of the same, and a method for inhibiting the reduction of the active-oxygen eliminating activity, and more particularly to a reduction inhibitory agent for active-oxygen eliminating activity, which comprises trehalose as an effective ingredient, uses of the same as compositions obtainable by incorporating the inhibitory agent into plant edible substances and/or plant antioxidants, and a method for inhibiting the reduction of active-oxygen eliminating activity of plant substances.

2. Description of the Prior Art

It is well known that plant edible substances such as vegetables, mushrooms, and layers are important for living bodies as sources of functional ingredients such as vitamins, minerals, and edible fibers, and are essential food materials for the growth of living bodies. Recently, these edible plants have become to be more focused on their active-oxygen eliminating activity that relates deeply to the maintenance and promotion of health, the prevention of aging and geriatric diseases, and the inhibition of carcinogenesis. Mechanism for the cause of aging of living bodies and related diseases thereof such as cancers, arteriosclerosis, liver cirrhosis, myocardial infarction, cerebral apoplexy, cataract, Parkinson disease, rheumatism, and Alzheimer's dementia as incurable diseases are still remained unknown in many aspects. However, the mechanism of such incurable diseases has come to be considered; active-oxygens such as superoxide which is an oxygen having unpaired electron and relatively-high reactivity, and its derivatives including hydroxyradical and hydrogen peroxide oxidize, oxidize intracellular target molecules such as membrane lipids, proteins, and DNAs to induce oxygen-related defective and to cause aging of living bodies and related diseases thereof.

Enzymes capable of eliminating active-oxygen such as superoxide dismutase (EC 1.15.1.1) and catalase (EC 1.11.1.6), and antioxidants such as L-ascorbic acid and α-tocopherol exist in living cells, and the concentration of intracellular active-oxygen is kept generally to an extremely-low level. However, it is considered that irradiation of relatively-large amount of ultraviolet rays, radiations, and magnetic waves; excessive physical exercises; strong mental stresses; and aging would form active-oxygen in an amount that can not be eliminated by active-oxygen-eliminating activity of living bodies, resulting in an accumulation of compounds oxidized by the excessive amount of active-oxygen and causing the aforesaid oxygen-related defective. To improve the problem, for example, Japanese Patent Kokai Nos. 168,435/93 and 143,466/96 proposed methods which comprise supplementing to living bodies active-oxygen eliminating activity, which is easy to shortage, to promote the maintenance and promotion of health of living bodies by using a relatively-high active-oxygen eliminating activity of edible plants. It was confirmed that even if such edible plants were used, processings such as juice extracting, extracting, heating, and drying, and successive storage conditions for the plants may lower the inherent active-oxygen eliminating activity or even extinguish the activity completely. It has been expected to establish a novel method for inhibiting the reduction of active-oxygen eliminating activity without causing serious side effects in living bodies.

SUMMARY OF THE INVENTION

The object of the present invention is to provide a novel reduction inhibitory agent for active-oxygen eliminating activity, a composition obtainable by incorporating the agent into plant edible substances and/or plant antioxidants to inhibit their active-oxygen eliminating activity, and a method for inhibiting the reduction of active-oxygen eliminating activity of the plant edible substance and/or the plant antioxidants.

To attain the above objects, the present inventors studied for the utilization of saccharides, and continued studying; they examined the influence of reduction inhibitory effect on active-oxygen eliminating activity of plant substances with active-oxygen eliminating activity such as plant edible substances and plant antioxidants by incorporating saccharides thereunto.

As a result, they found that trehalose exerts a more effective activity than other saccharides and inhibits strongly the reduction of plant active-oxygen eliminating activity, and accomplished this invention.

The first object of the present invention is to provide a reduction inhibitory agent for active-oxygen eliminating activity which comprises trehalose as an effective ingredient; the second object of the present invention is to provide a composition obtainable by incorporating the agent into plant edible substances and/or plant antioxidants with active-oxygen eliminating activity to inhibit the reduction of their active-oxygen eliminating activity; and the third object of the present invention is to provide a method for inhibiting the reduction of plant active-oxygen eliminating activity, which comprises incorporating the agent into plant substances with active-oxygen eliminating activity.

DETAILED DESCRIPTION OF THE INVENTION

The trehalose suitably used as an effective ingredient in the present reduction inhibitory agent for active-oxygen eliminating activity is α,α-trehalose, and any trehaloses can be used in the present invention independently of their origins and sources, as long as they inhibit the reduction of active-oxygen eliminating activity. For example, trehaloses prepared from yeasts as disclosed in Japanese Patent Kokai No. 246,097/95, from maltose as disclosed in Japanese Patent Kokai Nos. 216,695/83 and 170,977/95, and from starch as disclosed in Japanese Patent Kokai Nos. 143,876/95 and 213,283/95 can be arbitrarily used in the present invention. Any types of trehalose in the form of a syrup, crystalline powder of massecuite, crystalline hydrate, crystalline anhydride, or amorphous solid can be arbitrarily used. Commercially-available high-purity crystalline trehalose hydrate and crystalline trehalose anhydride can be arbitrarily used. The trehalose content in the present reduction inhibitory agent for active-oxygen eliminating activity can be selected from those which can allow to exert a desired reduction inhibitory activity on the active-oxygen eliminating activity of plant edible substances, etc.; usually, at least about 20 w/w % (throughout the present specification, the wording "w/w %" will be abbreviated as "%", unless specified otherwise) to the agent, on a dry solid basis (d.s.b.), and preferably at least 50%, d.s.b. The present reduction inhibitory agent can be suitably incorporated into compositions containing plant edible substances and/or plant antioxidants in an amount of, usually, at least one percent, preferably, at least about 5 percent, and more preferably at least 20%, d.s.b.

The wording "incorporating" as referred to in the present invention means "coexisting"; in the case of incorporating the present reduction inhibitory agent into plant substances with active-oxygen eliminating activity, any coexisting methods can be acceptable as long as they can allow to impart satisfactory reduction inhibitory activity for plant active-oxygen eliminating activity independently of the incorporation methods and relative proportions. The present agent can be preferably incorporated into plant edible substances and/or plant antioxidants by allowing the agent to contact with the substances and/or the antioxidants in aqueous systems as homogeneity as possible. For example, in the case of using plant edible substances, etc., in a juicy form such as a liquid or suspension form, the present agent in the form of a powder, crystal, or solid can be incorporated into the plant edible substances as homogeneity as possible by mixing with and dissolving in the substances. While in the case of using plant edible substances and plant antioxidants in a solid form, they are treated with water to give a juicy form such as a liquid or suspension form, and incorporated with the present agent by either employing the above method or providing successively a syrup of the present agent, and either dispersing, dissolving or suspending the plant edible substances and antioxidants in the syrup to allow to contact them with the agent as homogeneity as possible and to incorporate the agent into the substances and antioxidants. In the case of using plant edible substances such as disruptant of raw plant-tissues, the present agent can be incorporated into the plant edible substances either by sprinkling over the substances and mixing them to dissolve the present agent in the substances, or by soaking the plant edible substances in the present agent in a syrup form.

The plant substances with active-oxygen eliminating activity usable in the present invention include edible plants per se; disrupted, minced, pulverized, dried, and extracted products of edible parts of the edible plants; and/or plant antioxidants. Examples of the edible plants suitably used in the present invention are edible rootcrops such as carrots, lotus roots, onions, burdocks, Japanese radishes, taros, and yams; leaf vegetables such as lettuces, chicories, Chinese cabbages, cabbages, kales, moroheiya or *Corchorus olitorius, Angelica keiskei,* spinach, Malabar nightshades, komatsuna (a kind of Chinese cabbage), nozawana (a kind of turnip), *Chrysanthemum coronarium,* chingensai (a chinese vegetable), and turnips; fruit vegetables such as okura or gumbos, cauliflowers, broccolis, eggplants, tomatos, cucumbers, pumpkins, zucchini, green peppers, field peas, and kidney beans; vegetables such as alfalfa, bean sprouts including those of soy beans and mung beans; mushrooms such as shiitake mushrooms, winter mushrooms or *Celtis sinensis,* and shimeji mushrooms; seaweeds such as hijiki seaweed or *Hijikia fusiformis,* wakame seaweed or *Undaria pinnatifida,* and tangs; citrus fruits such as lemons, citrons, and sudachi (a kind of citrus fruit), shaddocks, and kumquats; fruits such as bananas, kiwifruits, strawberries, hawthorns, blueberries, grapes, peaches, apples, pears, chestnuts; herbs such as garlics, gingers, wasabis (a Japanese horseradish), mustards, parsleys, Chinese parsleys, beefsteak plants, leeks, Welsh onions, celeries, dropworts, cressons, Guinea peppers, Japanese peppers, peppers, rosemaries, and mints; medicinal herbs and crude drugs such as mugworts, common plantains, bad-smelling perennial plants of the family Saururaceae, *Cassia obtusifolia,* Japanese green gentians, aloes, licorices, turmerics, Japanese indigo plants, *Pfaffia,* loquat leaves, field horsetails, pine needles, bamboo leaves, umes or Japanese apricots, tea leaves, barley leaves, wheat leaves, oats leaves, rye leaves, buckwheat leaves, ginkgo leaves, Chinese gutta percha leaves, oobanasarusuberi (a plant of the family Lythrum), *Aspalathus linearis,* and *Gymnema sylvestre;* and others including edible parts of nuts, seeds, and germs such as adlays, buckwheats, sesames, rices, wheats, corns, broad beans, soybeans, peanuts, walnuts, pine seeds, and other seeds and germs.

One or more of the following relatively-low-molecular-weight plant antioxidants can be suitably selected and used as the present plant antioxidants: Plant enzymes having active-oxygen eliminating activity such as superoxide dismutase, catalase, and superoxide; plant pigments such as rutin, α-glucosyl rutin, hesperidin, α-glucosyl hesperidin, naringin, α-glucosyl naringin, chlorophyll, carotenoid, and anthocyanin; plant polyphenols such as gallic acid, catechin, α-glucosyl catechin, and tannic acid; and plant vitamins such as α-tocopherol, L-ascorbic acid, and riboflavin. In the present invention, the relatively-low-molecular-weight plant antioxidants can be contained in the edible plants, or added supplementarily to the contents during the processing of the edible parts of edible plants. The plant antioxidants which exist separately to the edible plants, can be used in the present invention. The plant antioxidants should not be restricted to those which are extracted from plants and include those which are artificially synthesized and produced.

Explaining more concretely, processes for producing the present composition, which the reduction of the active-oxygen eliminating activity is satisfactorily inhibited, are as follows: Edible parts of edible plants are, for example (i) disrupted or cut by mixers, juicers, or pulverizes into pastes or suspensions, into which the present agent is incorporated by adding thereto and dissolving therein; or (ii) extracted with solvents such as hot water and alcohols, and filtered, if necessary, further concentrated into liquids or pastes, followed by incorporating the present agent into the liquids or pastes by mixing to dissolve therein. The compositions thus obtained are usually syrupy, pasty, or juicy disrupted products which have a relatively-high moisture content and require a relatively-low storage temperature for a satisfactory shelf-life. The compositions can be dried and/or pulverized, or dried and/or pulverized after sterilization by heating to obtain powdery or small pieces of solid compositions. Conventional drying and pulverizing methods can be arbitrarily used in the present invention; the compositions of syrupy, pasty, or juicy disrupted products can be (i) successively dried in vacuo, air-dried, drum-dried, pulverized, and sieved; (ii) successively spray-dried, subjected to fluidized-drying, and sieved; or (iii) successively mixed with anhydrous saccharides such as maltose or trehalose anhydride to effect dehydration, dried, and sieved into powdery products. If necessary, the powdery products can be arbitrarily granulated, tabletted, and capsulated into appropriate shapes and forms in use. The solid compositions, processed up to such a high-level, will acquire more improved activity for inhibiting the reduction of active-oxygen eliminating activity, storage stability, and handleability. The solid compositions containing edible plant substances have features that they inhibit effectively the deterioration of plant pigments, contained in the material edible plants, such as chlorophylls, carotenoids, anthocyanin, and flavonoids; retain satisfactorily the inherent color of the pigments; and mask unfavorable tastes such as bitterness and astringency.

The present composition, containing trehalose and a plant edible substance or plant antioxidant and having inhibitory activity for the reduction of active-oxygen eliminating activity, can be further mixed with one or more appropriate substances in the form of a solid or liquid such as essential minerals, edible fibers, saccharides for promoting the growth of bifid bacteria, vitamins, biologically active substances, and preservatives.

The essential minerals usable in the present include, for example, calcium, magnesium, phosphorus, iron, copper, zinc, and cobalt, and these minerals are used in an adequate amount. The edible fibers satisfactorily usable in the present invention are, for example, pectin, alginic acid, carrageenan, gum arabic, glucomannan, cyclodextrin, and pullulan. It was revealed that among the edible fibers, particularly pullulan exerts a strong reduction-inhibitory-activity for plant active-oxygen eliminating activity when used in combination with trehalose as the effective ingredient according to the present invention. Based on this, pullulan can be most satisfactorily used together with trehalose in the present agent and used in the production of the present compositions.

Examples of the saccharides used for promoting the growth of bifid bacteria in the present invention are lactosucrose, fructooligosaccharide, galactooligosaccharide, and isomaltooligosaccharide which can be arbitrarily used on demands.

The vitamins satisfactorily usable in the present invention include, for example, water-soluble vitamins such as thiamin, riboflavin, L-ascorbic acid, rutin, hesperidin; naringin, niacin, pyridoxine, cyanocobalamine, and derivatives thereof; and lipid-soluble vitamins such as vitamin A, vitamin D, α-tocopherol, vitamin K, and derivatives thereof.

One or more of biological active substances such as hormones, antibiotics, cytokines, and propolis can be arbitrarily used on demands. Adequate amounts of ethanol, acetic acid, lactic acid, and salt can be arbitrarily used on demands as preservatives in the present invention.

To improve the quality of the present compositions and other compositions containing the present compositions, adequate coloring agents, flavoring agents, taste-imparting agents, stabilizers, fillers, adjuvants, and excipients can be arbitrarily used.

The compositions thus obtained have at least five units/g composition, d.s.b., and more preferably, at least 10 units/g composition, d.s.b., of active-oxygen eliminating activity as determined by the nitroblue tetrazolium (NBT) test, and they can be arbitrarily and easily administered to subjects via appropriate routes of oral, intubational, percutaneous, and permucosal administrations to impart active-oxygen eliminating activity with lesser deterioration of their quality. Intake of the present composition containing plant edible substances enriches plant functional ingredients such as vitamins, minerals, and edible fibers inherent to the plants, and enriches living bodies with active-oxygen eliminating activity. Thus the present composition can be satisfactorily used to maintain and promote your health, prevent aging and geriatric diseases, promote the treatment of incurable diseases, and to inhibit carcinogenesis; and arbitrarily used as food products, cosmetics, pharmaceuticals, and their materials and processing intermediates.

To enrich nutritional value and improve qualities, taste, and taste-preference, the present composition can be arbitrarily used for health food products and other food products in general, for example, seasonings such as "furikake" (a seasoned fish meal), sauces, ketchup, "yakiniku-no-tare" (a sauce for Japanese grilled meat), curry roux, and instant soup mixes; Japanese and Western cakes such as "mochi" (a rice paste), "dango" (a ball of rice paste), candies, chewing gums, backed confectioneries, snack confectioneries, waffles, sponge cakes, buns, and bakeries; frozen desserts such as ice creams, sherbets, and candies; pastes such as fruit pastes, fruit sources, peanut pastes, and raw jams; pickles and pickled products; meat products such as hams and sausages; products of fish meats such as "kamaboko" (a steamed fish paste), "chikuwa" (a kind of fish paste), "hanpen" (a fish cake), and sausages; "chinmi" (a delicacy); "tsukudani" (a food boiled down in soy); daily dishes; beverages such as vegetable juices, fruit juices, and carbonated beverages; rice products such as rice gruels, porridges of rice and vegetables, and cooked rice with seasonings, meats, and vegetables; noodles such as iced noodles, macaronis, and pastas; food products such as mix for pudding, premixes for hot cakes, instant juices, instant soups, and frozen foods; and their materials and processing intermediates. The present composition can be arbitrarily used in cosmetics such as skin-beautifying agents, packs, creams, shampoos, hair rinses, hair tonics, bath salts, enzymic agents, and tooth pastes in the form of a liquid, paste, powder, or granule; and used as a material or a processing intermediate for those products. Furthermore, the present composition can be used to treat and prevent aging-related diseases in the form of an oral and/or intubation nutrient or therapeutic agent such as a collunarium, nebula, digestive agent, stomachic, enzymic agent, ointment, cataplasm, and their materials and processing intermediates.

The present composition consists substantially of food materials and can be used with less fear of causing toxicity. Usually it can be suitably used on a dry solid basis at a dose of about 0.1 to 1,000 g/adult/day, preferably, about 0.2 to 500 g/adult/day, and more preferably, about 1 to 100 g/adult/day when administered to subjects orally. The present composition can be applied to subjects intubationally, percutaneously, and permucosally in accordance with the dose of the oral administration.

The following experiments describe the present invention in detail:

Experiment 1

Influence of Saccharides on Reduction Inhibitory Activity for Active-Oxygen Eliminating Activity Fresh raw carrots were disrupted by a mixer, and 10% of either of saccharides, d.s.b., was added to the mixture and dissolved therein. The solution was dried under reduced pressures at 40° C. for two days, dried in vacuo at the same temperature for 24 hours, and pulverized by a mixer into a powdery carrot composition. The saccharides used were commercialized reagents of glucose, mannitol, sorbitol, maltose, sucrose, trehalose, and pullulan. An about 100 g of the composition was placed and sealed in a 500-ml polystyrene container, and stored at 40° C. for seven days. The active-oxygen eliminating activity of the composition before and after the storage were compared. The assay for the active-oxygen eliminating activity followed the nitroblue tetrazolium test by Toshio IMANARI et at in *Igakuno Ayumi,* Vol. 101, pp. 496–497 (1977); the level of superoxide, formed in a xanthine-xanthine oxidase system, was assayed by quantifying calorimetrically the content of formazan formed by reducing NBT. As a control, refined water was used as a test solution. One unit activity of active-oxygen eliminating activity is defined as that inhibits 50% formazan formation as compared with the control. Table 1 shows the composition of the powdery compositions, and the active-oxygen eliminating activity per gram of either of the compositions before and after the storage. As evident from Table 1, among the saccharides tested the composition with trehalose showed the highest residual percentage for active-oxygen eliminating activity, revealing that trehalose exerts a strong effect on the reduction inhibitory activity for active-oxygen eliminating activity. The reduction inhibitory activity of trehalose was strongly higher than that of glucose as the constituent saccharide for trehalose, and that of maltose as a disaccharide consisting of two glucose units similar to trehalose. Thus trehalose is suitably used as an effective ingredient for a reduction inhibitory agent for active-oxygen eliminating activity. Next to trehalose, pullulan showed a relatively-high reduction inhibitory activity for active-oxygen eliminating activity.

TABLE 1

| Saccharide | Composition of powdery composition (%) | | | Saccharide content (d.s.b.) (%) | Activity (unit/g) | | Percentage of residual activity (%) |
|---|---|---|---|---|---|---|---|
| | Carrot | Saccharide | Moisture | | Before storage | After storage | |
| None | 93.4 | 0.0 | 6.6 | 0.0 | 870 | 100 | 11 |
| Glucose | 48.8 | 46.4 | 4.8 | 48.7 | 580 | 170 | 29 |
| Mannitol | 49.8 | 47.5 | 2.7 | 48.8 | 520 | 59 | 11 |
| Sorbitol | 48.2 | 46.0 | 5.8 | 48.8 | 560 | 26 | 5 |
| Maltose | 48.1 | 45.8 | 6.1 | 48.8 | 550 | 180 | 33 |
| Sucrose | 48.2 | 46.0 | 5.8 | 48.8 | 660 | 180 | 27 |
| Trehalose | 47.9 | 45.7 | 6.4 | 48.8 | 580 | 380 | 66 |
| Pullulan | 47.7 | 45.5 | 6.8 | 48.8 | 710 | 360 | 51 |

Experiment 2

Influence of Trehalose Concentration on Reduction Inhibitory Activity for Active-Oxygen Eliminating Activity Similarly as in Experiment 1, 0–20% of trehalose, d.s.b., was mixed with and dissolved in a disrupted carrot. The resulting each mixture was dried in vacuo at 40° C. for 24 hours, and pulverized into a powdery carrot composition. Similarly as in Experiment 1, each powdery composition was placed and sealed in a polystyrene container, and stored at 40° C. for seven days for evaluating the reduction inhibitory activity for active-oxygen eliminating activity. Table 2 shows the active-oxygen eliminating activity of one gram of each powdery composition before and after the storage. Based on the data from Table 2, at least of about one percent, preferably, at least of about five percent, and more preferably, at least of about 20% of trehalose, d.s.b., exerted a desired effective reducing inhibitory activity for active-oxygen eliminating activity.

Experiment 3

Influence of Trehalose on Reducing Inhibitory Activity for Active-Oxygen Eliminating Activity of Vegetables Vegetables were treated similarly as in Experiment 1, and 10% trehalose, d.s.b., to the disrupted vegetables. The resulting each mixture was dried in vacuo at 45° C. for 20 hours, and pulverized into a powdery vegetable composition. Similarly as in Experiment 1, each compositions was respectively placed in a container and stored at 40° C. for six days. The active-oxygen eliminating activity of one gram of each composition before and after the storage was compared with that of the composition prepared without trehalose. Table 3 shows the composition of the powdery compositions, and their active-oxygen eliminating activity. Reduction inhibitory activity for active-oxygen eliminating activity by incorporation of trehalose was observed in vegetables such as carrot, onion, Japanese radish, cabbage, spinach, cucumber, and pumpkin.

TABLE 2

| Percentage (%) of trehalose added to carrot | Composition of powdery composition (%) | | | Trehalose content (d.s.b) (%) | Activity (unit/g) | | Percentage of residual activity (%) |
|---|---|---|---|---|---|---|---|
| | Carrot | Trehalose | Moisture | | Before storage | After storage | |
| 0.0 | 95.3 | 0.0 | 4.7 | 0.0 | 940 | 330 | 35 |
| 0.1 | 94.3 | 1.0 | 4.7 | 1.0 | 930 | 400 | 43 |
| 0.5 | 90.4 | 4.7 | 4.9 | 4.9 | 750 | 460 | 61 |
| 1.0 | 85.9 | 8.9 | 5.2 | 9.4 | 860 | 480 | 56 |
| 2.5 | 75.3 | 19.6 | 5.1 | 20.7 | 700 | 460 | 66 |
| 5.0 | 62.3 | 32.4 | 5.3 | 34.2 | 600 | 370 | 62 |
| 10.0 | 46.1 | 48.1 | 5.8 | 51.1 | 400 | 330 | 83 |
| 20.0 | 30.3 | 63.1 | 6.6 | 67.6 | 380 | 240 | 63 |

TABLE 3

| Vegetable (moisture (%)) | Composition of powdery composition (%) Carrot | Saccharide | Moisture | Trehalose content (d.s.b.) (%) | Activity (unit/g) Before storage | After storage | Percentage of residual activity (%) |
|---|---|---|---|---|---|---|---|
| Carrot | 94.5 | 0.0 | 5.5 | 0.0 | 1200 | 370 | 31 |
| (90.1) | 46.2 | 46.6 | 7.2 | 50.2 | 570 | 460 | 81 |
| Onion | 93.2 | 0.0 | 6.8 | 0.0 | 440 | 210 | 48 |
| (89.3) | 47.5 | 44.3 | 8.2 | 48.3 | 300 | 230 | 77 |
| Japanese radish | 92.7 | 0.0 | 7.3 | 0.0 | 1100 | 630 | 57 |
| (94.0) | 35.0 | 58.3 | 6.7 | 62.5 | 530 | 450 | 85 |
| Cabbage | 94.8 | 0.0 | 5.2 | 0.0 | 4100 | 2500 | 63 |
| (93.8) | 35.7 | 57.5 | 6.8 | 61.7 | 1600 | 1400 | 88 |
| Spinach | 93.2 | 0.0 | 6.8 | 0.0 | 3500 | 1300 | 36 |
| (94.1) | 34.4 | 58.4 | 7.2 | 62.9 | 1200 | 890 | 74 |
| Eggplant | 91.5 | 0.0 | 8.5 | 0.0 | 38000 | 31000 | 82 |
| (93.7) | 34.8 | 55.3 | 9.9 | 61.4 | 13000 | 11000 | 85 |
| Cucumber | 92.7 | 0.0 | 7.3 | 0.0 | 4600 | 1300 | 30 |
| (95.0) | 30.3 | 60.5 | 9.2 | 66.6 | 1900 | 1100 | 58 |
| Pumpkin | 93.2 | 0.0 | 6.8 | 0.0 | 1600 | 610 | 38 |
| (84.0) | 56.2 | 35.2 | 8.6 | 38.5 | 880 | 460 | 52 |

Experiment 4

Reduction Inhibitory Activity for Active-Oxygen Eliminating Activity by Trehalose with Respect to Superoxide Dismutase and Antioxidants In one milliliter of a 45 w/v % trehalose solution was dissolved five micrograms of superoxide dismutase from a horseradish-commercialized by Sigma Chemical Co., St. Louise, USA, 10 mg α-glucosyl hesperidin commercialized by Hayashibara Biochemical Laboratories, Inc., Okayama, Japan, 10 mg α-glucosyl rutin commercialized by Hayashibara Biochemical Laboratories, Inc., Okayama, Japan, 250 μg gallic acid commercialized by Wako Pure Chemical Industries, Ltd., Tokyo, Japan, or 50 μg catechin to obtain a liquid composition. Each of the compositions was placed in a glass test tube, sealed with a rubber cap, and stored under light-shielded conditions. As a control, water was used in place of the trehalose solution. Table 4 shows the active-oxygen eliminating activity before and after the storage. As shown in Table 4, it was confirmed that trehalose exerts an effective reducing inhibitory activity for active-oxygen eliminating activity of plant antioxidants such as superoxide dismutase, α-glucosyl hesperidin, α-glucosyl rutin gallic acid, and catechin. Mere mixing of a powdery crystalline trehalose hydrate and either of the powdery antioxidants into a powdery mixture, almost no change of the active-oxygen eliminating activity was observed when subjected to storage test similarly as above. Based on the results, it was revealed that a reducing inhibitory agent for active-oxygen eliminating activity, which comprises trehalose as an effective ingredient, could scarcely exert the desired activity only when mixed in a powder form with powdery substances having active-oxygen eliminating activity, but exert the desired activity when trehalose in a melted state is allowed to contact with and incorporated into the substances, or when trehalose is incorporated into the substances in an aqueous system.

TABLE 4

| Content of antioxidant | Storage condition | Trehalose concentration (%) | Activity (unit/mg antioxidant) Before storage | After storage | Residual activity (%) |
|---|---|---|---|---|---|
| Superoxide dismutase (5 μg/ml) | 60° C. 17 hours | 0 45 | 10,000 11,000 | 4,600 9,400 | 46 85 |
| α-Glucosyl hesperidin (10 mg/ml) | 80° C. 5 days | 0 45 | 3.8 3.6 | 1.0 2.4 | 26 67 |
| α-Glucosyl rutin (10 mg/ml) | 80° C. 5 days | 0 45 | 25 26 | 18 22 | 72 85 |
| Gallic acid (250 μg/ml) | 80° C. 5 days | 0 45 | 590 570 | 390 470 | 66 82 |
| Catechin (50 μg/ml) | 25° C. 20 hours | 0 45 | 470 380 | 2.2 310 | 0 82 |

Experiment 5

Reduction Inhibitory Effect for Active-Oxygen Eliminating Activity on Herb Extracts Ten liters of water was added to 500 g of a dried specimen of plantain, *Plantago asiatica*, commercialized by Daido Seiyaku Co., Ltd., Tokyo, Japan, and the mixture was infused for 90 min, followed by collecting a supernatant of the infused solution by a basket-type centrifuge. The supernatant was boiled down to obtain two kilograms of an about 5 w/v % solution. Two hundred and forty grams of trehalose and 10 g of pullulan, d.s.b., were mixed with and dissolved in one kilogram of the above concentrate, and the solution was spray dried by "SD-1", a portable spray-dryer commercialized by Tokyo Rika Mfg. Co., Ltd., Tokyo, Japan, Tokyo, Japan, into a composition containing an extract of *Plantago asiatica*. As a control, using dextrin with DE (dextrose equivalent) of about 11 in place of the trehalose and pullulan, a powdery composition similar to the above composition was prepared. Similarly as in Experiment 1, these powdery compositions were placed in polystyrene containers, sealed, and stored at 40° C. for seven days for examining the reduction inhibitory effect for active-oxygen eliminating activity. Both the compositions had an activity of about 5,000 units/g composition before the storage. On seven days after the storage, the composition with trehalose and pullulan had an activity of about 4,300 units/g composition, while the composition with dextrin had an activity of about 3,100 units/g composition. The data shows that the use of trehalose and pullulan exerts a higher reduction inhibitory effect for active-oxygen eliminating activity than in the case of using dextrin.

The following Examples describe the present invention; Examples A describe the present reducing inhibitory agent for active-oxygen eliminating activity, and Examples B describe the present composition where the reduction of active-oxygen eliminating activity is satisfactorily inhibited:

EXAMPLE A-1

Reduction Inhibitory Agent for Active-Oxygen Eliminating Activity

Corn starch was prepared into an about 33% starch suspension which was then mixed with 0.1% calcium carbonate, adjusted to Ph 6.5, mixed with 0.3% per g starch of "TERMAMYL", an α-amylase specimen commercialized by Novo Industri A/S Copenhagen, Denmark, enzymatically reacted at 95° C. for 15 min, autoclaved at 120° C., and promptly cooled to obtain a liquefied solution with DE of about four. Thereafter, the liquefied solution was admixed with four units/g starch, d.s.b., of respective non-reducing saccharide-forming enzyme and trehalose-releasing enzyme, prepared by culturing a microorganism of the genus *Rhizobium* by the method in Japanese Patent Kokai No. 213,283/95, 500 units/g starch of isoamylase, and five units/g starch of cyclomaltodextrin glucanotransferase, adjusted to Ph 6.2, and enzymatically reacted at 40° C. for 48 hours. The reaction mixture was heated to inactivate the remaining enzymes, then admixed with 10 units/g substrate of glucoamylase and enzymatically reacted at pH 5.0 and 50° C. for 10 hours. The reaction mixture thus obtained contained about 86% trehalose, d.s.b. The mixture was heated to inactivate the remaining enzyme, then in a conventional manner purified by decoloring and desalting, and continuously crystallized while concentrating. The resulting massecuite was separated by a basket-type centrifuge, and the crystal was washed by spraying with a small amount of water to obtain a crystalline trehalose hydrate with a purity of 98% or higher in a yield of about 64%, d.s.b. The product is a crystalline trehalose hydrate with a considerably-high purity and suitably used as the present reduction inhibitory agent and advantageously used to inhibit the reduction of active-oxygen eliminating activity of plant edible substances.

EXAMPLE A-2

Reduction Inhibitory Agent for Active-Oxygen Eliminating Activity

A microorganism of the genus *Thermus* capable of producing a maltose/trehalose converting enzyme was cultured in a nutrient culture medium by the method in Japanese Patent Kokai No. 170,977/95. After completion of the culture, the proliferated cells were collected by centrifugation to obtain 250 g wet cells having a total activity of about 7,500 units. The cells were immobilized using sodium alginate solution and calcium chloride solution to obtain alginic acid-immobilized cells. A jacketed-glass column, 5.4 cm in diameter and 100 cm in length, injected with the immobilized cells, and kept at 60° C. A 40% maltose solution (pH 6.5) was fed to the column at SV (space velocity) 0.2 by the descending method to obtain a reaction mixture containing about 66% trehalose, about 28% maltose, and about 6% glucose. The reaction mixture was in a conventional manner purified by decoloring and desalting, concentrated in vacuo into an about 75% syrup which was then placed in a crystallizer, admixed with about one percent of respective seed crystals of crystalline trehalose hydrate and crystalline maltose hydrate, and cooled to obtain a massecuite with a crystallization degree of about 25%. The massecuite was spray dried and aged to obtain a powdery crystalline saccharide in a yield of about 92% to the material maltose, d.s.b. The powdery saccharide is a stable powdery saccharide, which has a crystallization degree of about 60% and contains about 66% trehalose, about 28% maltose, and about six % glucose, and it can be suitably used as a reduction inhibitory agent for active-oxygen eliminating activity and arbitrarily used to inhibit the reduction of active-oxygen eliminating activity of plant edible substances.

EXAMPLE A-3

Reduction Inhibitory Agent for Active-Oxygen Eliminating Activity

Potato starch was prepared into a 10% starch suspension which was then subjected to the action of α-amylase to obtain a liquefied solution. To the liquefied solution were added three units/g starch, d.s.b., of a non-reducing saccharide-forming enzyme disclosed in Japanese Patent Kokai No. 213,283/95, five units/g starch, d.s.b., of a trehalose-releasing enzyme, 1,000 units/g starch, d.s.b., of an isoamylase, and one unit/g starch, d.s.b., of a maltotetraose-forming amylase, and the mixture was enzymatically reacted at pH 6.0 and 40° C. for 48 hours. The reaction mixture was heated to inactivate the remaining enzyme, and in a conventional manner purified by decoloring and desalting and concentrated in vacuo to obtain a syrup with a moisture content of about 30% and DE of about 15 in a yield of about 90%, d.s.b. The product is a stable syrup, which contains, on a dry solid basis, about 50% trehalose along with other saccharides derived from starch, can be suitably used as a reduction inhibitory agent for active-oxygen eliminating activity, and arbitrarily used to inhibit the reduction of active-oxygen eliminating activity of plant edible substances.

EXAMPLE A-4

Reduction Inhibitory Agent for Active-Oxygen Eliminating Activity

One hundred parts by weight of a high-purity crystalline trehalose hydrate, obtained by the method in Example A-1, was mixed to homogeneity with one part by weight of pullulan to produce a solid reduction inhibitory agent for active-oxygen eliminating activity. The product can be arbitrarily used in a reduction inhibitory agent for active-oxygen eliminating activity of plant edible substances.

EXAMPLE A-5

Reduction Inhibitory Agent for Active-Oxygen Eliminating Activity

In 100 hundred parts by weight of a trehalose syrup, obtained by the method in Example A-3, was dissolved by mixing to homogeneity 0.5 part by weight of pullulan, and 0.5 part by weight of a readily-water-soluble cyclodextrin into a syrupy reduction inhibitory agent for active-oxygen eliminating activity. The product can be arbitrarily used in a reduction inhibitory agent for active-oxygen eliminating activity of plant edible substances.

EXAMPLE B-1

Composition Containing Spinach

Fresh spinach was pulverized by a mixer, and in 10 parts by weight of the resulting disruptant were dissolved by mixing one part by weight of a reduction inhibitory agent for active-oxygen eliminating activity obtained by the method in Example A-4, and 0.1 part by weight of α-glucosyl rutin. The resulting mixture was heated at 100° C. for 10 min, dried with air heated to 40° C. for two hours, dried in vacuo at 40° C. for 16 hours, and powdered by a pulverizer to obtain a composition containing spinach having an active-oxygen eliminating activity of about 1,200 units/g composition.

The composition retained satisfactorily the inherent color of spinach and stimulated your appetite. Intake of the composition enriches living bodies with functional ingredients such as vitamins, minerals, and edible fibers inherent to the spinach, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-2

Composition Containing Cabbage

Cabbage was cut, branched, sliced by a cutter into fine strips in about 5 mm wide. Ten parts by weight of the fine strips was mixed with one part by weight of a reduction inhibitory agent for active-oxygen eliminating activity obtained by the method in Example A-3, and 0.05 part by weight of α-glucosyl rutin, and the mixture was allowed to stand at ambient temperature for two hours, then dried by air heated to 40° C. for two hours, dried in vacuo at 40° C. for 16 hours to obtain a composition containing fine strips of cabbage having an active-oxygen eliminating activity of about 1,300 units/g composition. The composition retained satisfactorily the inherent color of the cabbage and stimulated your appetite. Intake of the composition enriches living bodies with functional ingredients such as vitamins, minerals, and edible fibers inherent to the cabbage, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-3

Composition Containing Eggplant

A fresh eggplant was subjected to a slicer, and the sliced eggplant was washed with water. One part by weight of a reduction inhibitory agent for active-oxygen eliminating activity, obtained by the method in Example A-1, was mixed with and dissolved in 10 parts by weight of the sliced eggplant, and the resulting mixture was dried by air heated to 70° C. for two days to obtain a composition containing sliced eggplant having an active-oxygen eliminating activity of about 11,000 units/g composition. The composition retained the inherent color of the eggplant's skin and stimulated your appetite. Intake of the composition enriches living bodies with functional ingredients such as vitamins, minerals, and edible fibers inherent to the eggplant, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-4

Composition Containing Carrot

A fresh carrot was branched and sliced by a slicer. One part by weight of a reduction inhibitory agent for active-oxygen eliminating activity, obtained by the method in Example A-4, was added to 10 parts by weight of the sliced carrot and dissolved therein. The mixture was dried with air heated to 50° C. for 16 hours to obtain a composition containing sliced carrots having an active-oxygen eliminating activity of about 450 units/g composition. The composition satisfactorily retained the color inherent to the carrot, stimulated your appetite, and had a relatively-low hygroscopicity and a satisfactory shelf-life. Intake of the composition enriches living bodies with functional ingredients such as vitamins, minerals, and edible fibers inherent to the carrot, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-5

Composition Containing *Hizikia fusiforme*

Dried *Hizikia fusiforme* was swelled out in water and disrupted with a cutter. In 10 parts by weight of the disrupted mixture was dissolved by mixing five parts by weight of a reduction inhibitory agent for active-oxygen eliminating activity obtained by the method in Example A-2. The solution was dried by air heated to 50° C. for eight hours, dried in vacuo at 40° C., and pulverized into a composition containing *Hizikia fusiforme* having an active-oxygen eliminating activity of about 24 units/g composition. Intake of the composition enriches living bodies with functional ingredients such as vitamins, minerals, and edible fibers inherent to *Hizikia fusiforme,* and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-6

Composition Containing Shiitake Mushroom

A dried shiitake mushroom was swelled out in water, heated at 100° C. for 15 min, and disrupted by a cutter. In 100 parts by weight of the disrupted mixture was dissolved by mixing 0.1 part by weight of a tea extract and 10 parts by weight of a reduction inhibitory agent for active-oxygen eliminating activity obtained by the method in Example A-3, and the resulting mixture was dried at 50° C. for eight hours, dried in vacuo at 40° C., and pulverized to obtain a composition containing a powdery shiitake mushroom having an active-oxygen eliminating activity of about 560 units/g composition. Intake of the composition enriches living bodies with functional ingredients such as vitamins, minerals, and edible fibers inherent to *Hizikia fusiforme,* and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-7

Composition Containing Citron

Citron rind was disrupted by a cutter, and five parts by weight of the disrupted rind was mixed with one part by weight of a reduction inhibitory agent for active-oxygen eliminating activity, obtained by the method in Example A-1, to dissolve the agent therein. After preliminary freezing, the resulting mixture was freeze-dried for three days, and disrupted to obtain a composition containing a powdery citron having an active-oxygen eliminating activity of about 12 units/g composition. The composition retains satisfactorily the color and flavor inherent to the citron. Intake of the composition enriches living bodies with functional ingredients such as vitamins, minerals, and edible fibers inherent to the citron, and imparts the active-oxygen eliminating activity to living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-8

Composition Containing Ginger

A fresh ginger was disrupted by a mixer. In five parts by. weight of the disrupted mixture was dissolved by mixing one part by weight of an reduction inhibitory agent for active-oxygen eliminating activity obtained by the method in Example A-2. After preliminary freezing, the resulting mixture was freeze-dried for three days, and disrupted by a crusher to obtain a composition containing a powdery ginger having an active-oxygen eliminating activity of about 120 units/g composition. Intake of the composition enriches living bodies with functional ingredients such as vitamins, minerals, and edible fibers inherent to the ginger, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-9

Composition Containing Aojiso (a Beefsteak Plant)

Aojiso leaves were branched and disrupted by a mixer. In five parts by weight of the disrupted mixture was dissolved by mixing one part by weight of a reduction inhibitory agent for active-oxygen eliminating activity obtained by the method in Example A-4, and 0.5 part by weight of α-glucosyl rutin, then mixed with 49 parts by weight of crystalline trehalose anhydride as a desiccant. The resulting mixture was allowed to stand at ambient temperature for one day and disrupted by a crusher to obtain a composition containing a powdery aojiso having an oxygen eliminating activity of about 230 units/g composition. The composition satisfactorily retained the color, flavor and taste of the aojiso, and stimulated your appetite. Intake of the composition enriches living bodies with functional ingredients such as vitamins, minerals, and edible fibers inherent to the aojiso, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-10

Composition Containing Mugwort

According to a conventional manner, mugwort was placed in a boiling water with an adequate amount of salt to remove harshness, dehydrated softly and disrupted by a crusher. Five parts by weight of the disrupted mixture was mixed with 0.05 part by weight of α-glucosyl rutin and 1.3 parts by weight of a reduction inhibitory agent for active-oxygen eliminating activity obtained by the method in Example A-5. The resulting mixture was dried by air heated to 50° C. for four hours, dried in vacuo at 40° C. for 16 hours, and disrupted to obtain a composition containing a powdery mugwort having an active-oxygen eliminating activity of about 780 units/g composition. The composition satisfactorily retained the color, flavor and taste of the mugwort, and stimulated your appetite. Intake of the composition enriches living bodies with functional ingredients such as vitamins, minerals, and edible fibers inherent to mugwort, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-11

Composition Containing Dokudami (a Bad-Smelling Perennial Plant of the Family Saururaceae A half part by weight of a dried dokudami was mixed with 10 parts by weight of water, and heated to boiling for 90 min. A supernatant of the infused solution was collected by a basket-type centrifuge and boiled down to obtain four parts by weight of an about five w/v % solution. Two parts by weight of the concentrate was mixed with 0.5 part by weight of a reduction inhibitory agent for active-oxygen eliminating activity obtained by the method in Example A-4, and the resulting solution was spray-dried in a conventional manner to obtain a composition containing a powdery dokudami extract having an active-oxygen eliminating activity of about 1,400 units/g. composition. The composition had a lesser unsatisfactory smell and taste inherent to the dokudami and could be more easily swallowable than conventional ones. Intake of the composition enriches living bodies with functional ingredients such as vitamins, minerals, and edible fibers inherent to the dokudami, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-12

Composition Containing Aloe

A fresh aloe was disrupted by a mixer, and 10 parts by weight of the disrupted aloe was mixed with 0.1 part by weight of a tea extract and one part by weight of a reduction inhibitory agent for active-oxygen eliminating activity obtained by the method in Example A-1. The resulting mixture was dried by air heated to 70° C. for two days and disrupted by a crusher to obtain a composition containing a powdery aloe having an active-oxygen eliminating activity of 5,800 units/g composition. The composition had a lesser astringency of the aloe and was more easily swallowable than conventional ones. Intake of the composition enriches living bodies with functional ingredients such as vitamins, minerals, and edible fibers inherent to the aloe, and imparts the active-oxygen eliminating activity to the living bodies. The composition can be satisfactorily used to maintain and promote your health, prevent aging and geriatric diseases, promote the treatment of incurable diseases, and prevent catcinogenesis. Thus the composition can be arbitrarily used as a food product, cosmetic, pharmaceutical, or their material or processing intermediate.

EXAMPLE B-13

Composition Containing Chinese Cabbage Preserved with Seasonings

A Chinese cabbage preserved with seasonings was subjected to a cutter. To 10 parts by weight of the cut product was added and dissolved therein one part by weight of a reduction inhibitory agent for active-oxygen eliminating activity obtained by the method in Example A-1, and the mixture was dried with air heated to 55° C. for 16 hours to obtain a composition containing small pieces of Chinese cabbage, preserved with seasonings, having an active-oxygen eliminating activity of about 5,400 units/g composition. The product retained the color tint of the Chinese cabbage. When you tasted the product in your mouth, the satisfactory taste and flavor spread throughout your mouth and stimulated your appetite. Intake of the composition enriches living bodies with functional ingredients such as vitamins, minerals, and edible fibers inherent to the Chinese cabbage, and augments the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate. The composition can be also used as a food product such as furikake, premix for onigiri (a rice ball), and soup for Chinese noodles, and as a health food, cosmetic, pharmaceutical, or their material or intermediate.

EXAMPLE B-14

Composition of Nozawana (a Kind of Turnip)

A pickled nozawana was subjected to a cuter. To 10 parts by weight of the cut product was added and dissolved therein one part by weight of a reduction inhibitory agent for active-oxygen eliminating activity obtained by the method in Example A-1. The mixture was dried with air heated to 55° C. for 16 hours to obtain a composition containing small pieces of pickled nozawana having an active-oxygen eliminating activity of about 2,600 units/g composition. The product retained the color tint of the pickled nozawana. When you tasted the product in your mouth, the satisfactory taste and flavor spread throughout your mouth and stimulated your appetite. Intake of the composition enriches living bodies with functional ingredients such as vitamins, minerals, and edible fibers inherent to the pickled nozawana, and augments the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-15

Composition of Korean Pickles of Chinese Cabbage

A Korean pickles of Chinese cabbage was subjected to a cuter. To 10 parts by weight of the cut product was added and dissolved therein one part by weight of a reduction inhibitory agent for active-oxygen eliminating activity obtained by the method in Example A-4. The mixture was dried with air heated to 55° C. for 16 hours to obtain a composition containing small pieces of pickled nozawana having an active-oxygen eliminating activity of about 1,600 units/g composition. The product retained the color tint of the Korean pickles of Chinese cabbage. When you tasted the product in your mouth, the satisfactory taste and flavor spread throughout your mouth and stimulated your appetite. Intake of the composition enriches living bodies with functional ingredients such as vitamins, minerals, and edible fibers inherent to the Korean pickles of Chinese cabbage, and augments the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-16

Composition Containing Soy Bean

Soy beans were soaked in five-fold volumes of water overnight, and drained. Ten parts by weight of the resulting soy beans was placed in a pun, mixed with 35 parts by weight of a reduction inhibitory agent for active-oxygen eliminating activity obtained by the method in Example A-1, and 35 parts by weight of water. The mixture was boiled over a mild fire up to give a concentration of about 70% as determined by a brix apparatus and to obtain boiled beans. The beans were placed in a basket and dried with air heated to 40° C. overnight to obtain a composition containing soy beans having an active-oxygen eliminating activity of about 25 units/g composition. The product retained the color tint of the boiled soy beans. When you tasted the product in your mouth, the satisfactory taste and flavor spread throughout your mouth and stimulated your appetite. In the product, there exists crystalline trehalose hydrate within the soy beans' tissues, and the hydrate well retained the tissues. The product was a solid food having satisfactory taste and biting property. Intake of the composition enriches living bodies with functional ingredients such as vitamins, minerals, and edible fibers inherent to the soy beans, and augments the active-oxygen eliminating activity to the living bodies. Thus the composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-17

Composition Containing Apple

Fresh apples were pealed and subjected to a slicer to obtain sliced apples, about 5 mm in thickness, which were then soaked for 30 min in an about 75% solution prepared by dissolving a reduction inhibitory agent for active-oxygen eliminating activity, obtained by the method in Example A-1, in water by heating at 80° C., placed in a basket, and dried at 35° C. overnight to obtain a composition containing apple having an active-oxygen eliminating activity of about 50 units/g composition. The product retained the color tint of the apple. When you tasted the product in your mouth, the satisfactory taste and flavor spread throughout your mouth and stimulated your appetite. In the product, there exists crystalline trehalose hydrate within the apple's tissues, and the hydrate well retained the tissues. The product was a solid food having satisfactory taste and biting property. Intake of the composition enriches living bodies with functional ingredients such as vitamins, minerals, and edible fibers inherent to the soy beans, and augments the active-oxygen eliminating activity to the living bodies. Thus the composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-18

Composition Containing Carrot

Fresh carrots were subjected to a slicer, and five parts by weight of the sliced carrots was placed in an about 73% syrup which was mildly boiling at about 105° C. and which had been prepared by dissolving by heating 140 parts by weight of a reduction inhibitory agent for active-oxygen eliminating activity, obtained by the method in Example A-1, in 60 parts by weight of water. The resulting mixture was continued concentrating by boiling up to give a temperature of about 110° C. for 20 min and up to be dehydrated by heating into a fried-like product. Thereafter, the product was placed in a basket, dried by air heated to 50° C. for five hours to obtain a composition containing sliced carrots having an active-oxygen eliminating activity of about 200 units/g composition. The composition was a fried-like product of carrot, to which crystalline trehalose hydrate adhered, and it retained the inherent color of the carrot and stimulated your appetite. The product had a relatively-low hygroscopicity, satisfactorily shelf-life, and desired handleability. Intake of the composition enriches living bodies with functional ingredients such as vitamins, minerals, and edible fibers inherent to the carrot, and imparts the active-oxygen eliminating activity to the living bodies. The composition can be satisfactorily used to maintain and promote your health, prevent aging and geriatric diseases, promote the treatment of incurable diseases, and prevent catcinogenesis. Thus the composition can be arbitrarily used as a food product, cosmetic, pharmaceutical, or their material or processing intermediate.

EXAMPLE B-19

Composition Containing Apple

Fresh apples were pealed and subjected to a slicer into sliced apples about 5 mm in thickness. Four parts by weight of the sliced apples was then placed in an about 80% syrup heated to about 110° C., which had been prepared by dissolving by heating in water 140 parts by weight of a reduction inhibitory agent for active-oxygen eliminating activity, obtained by the method in Example A-1, and continued concentrating by boiling up to give a temperature of about 114° C. for about 10 min and up to be dehydrated by heating into a fried-like product. Thereafter, the product was placed in a basket, dried by air heated to 35° C. overnight to obtain a composition containing sliced apples having an active-oxygen eliminating activity of about 30 units/g composition. The composition was a fried-like product of apple, to which crystalline trehalose hydrate adhered, and it retained the inherent color of the apple and stimulated your appetite. The product had a relatively-low hygroscopicity, satisfactorily shelf-life, and desired handleability. Intake of the composition enriches living bodies with functional ingredients such as vitamins, minerals, and edible fibers inherent to the apple, and imparts the active-oxygen eliminating activity to the living bodies. The composition can be satisfactorily used to maintain and promote your health, prevent aging and geriatric diseases, promote the treatment of incurable diseases, and prevent carcinogenesis. Thus the composition can be arbitrarily used as a food product, cosmetic, pharmaceutical, or their material or processing intermediate.

EXAMPLE B-20

Chewing Gum

Three parts by weight of a gum base was heated up to be softened, then mixed with six parts by weight of crystalline trehalose hydrate, one part by weight of a composition containing aojiso obtained by the method in Example B-9, and 0.01 part by weight of a tea extract. The resulting mixture was admixed with adequate amounts of a flavor and color, kneaded by a roll in a conventional manner, shaped and packaged into a product having an active-oxygen eliminating activity of over 120 units/g product. The product is a chewing gum with satisfactory texture, flavor, and taste. The product containing trehalose as a saccharide has characters that it is not easily assimilated by dental-caries-inducing microorganisms, and it less causes dental caries.

EXAMPLE B-21

Dango (a Rice Paste)

Ten parts by weight of glutinous rice starch was mixed with 12 parts by weight of water, and the mixture was gelatinized by heating, then kneaded with 0.5 part by weight of a composition containing mugwort obtained by the method in Example B-10. The mixture thus obtained was in a conventional manner shaped and packaged into a dango having an active-oxygen eliminating activity of over 12 units/g content. The product is a yomogi-dango, i.e., a rice paste with mugwort, having a satisfactory color tint of yomogi, flavor, taste, and biting property.

EXAMPLE B-22

Nutrition

A composition consisting of the following ingredients was prepared; 20 parts by weight of crystalline α-maltose, 1.1 parts by weight of glycine, 0.18 part by weight of sodium glutamate, 1.2 parts by weight of salt, one part by weight of citric acid, 0.4 part by weight of calcium lactate, 0.3 part by weight of a composition containing spinach obtained by the method in Example B-1, 0.01 part by weight of thiamine, and 0.01 part by weight of riboflavin. Twenty-four grams aliquots of the composition were injected into small laminated aluminum bags and heat sealed to obtain a nutrition for intubation having an active oxygen eliminating activity of over 12 units/g composition. One bag of the nutrition is dissolved in about 300–500 ml water, and the solution can be arbitrarily administered to subjects orally or to the subjects' nasal cavities, stomachs, and intestines as a parenteral liquid-supplemental-nutrition

EXAMPLE B-23

Cosmetic Cream

Two parts by weight of polyoxyethylene glycol monostearate, 5 parts by weight of glyceryl monostearate, self-emulsifying, 2.8 parts by weight of a composition containing aloe obtained by the method in Example B-12, 0.2 part by weight of α-glucosyl rutin, one part by weight of liquid petrolatum, 10 parts by weight of glyceryl. tri-2-ethylhexanoate, and an adequate amount of an antiseptic were dissolved by heating in a conventional manner. The resulting solution was admixed with two parts by weight of L-lactic acid, five parts by weight of 1,3-butylene glycol and 66 parts by weight of refined water, and the mixture thus obtained was emulsified by a homogenizer and admixed with an adequate amount of a flavor under stirring conditions to obtain a cosmetic cream having an active-oxygen eliminating activity of over 46 units/g product. The product can be arbitrarily used as a therapeutic or preventive agent for sunburn skin, skin-beautifying agent, skin-whitening agent, and agent for inhibiting skin-aging-phenomena such as chloasmas, freckles, pigmentation, and wrinkles.

EXAMPLE B-24

Bath Salt

A bath salt having an active oxygen eliminating activity of over 220 units/g product, was prepared by mixing 26 parts by weight of refined water and adequate amounts of a coloring agent and a flavoring agent with 21 parts by weight of sodium DL-lactate, eight parts by weight of sodium pyruvate, five parts by weight of a composition containing citron obtained by the method in Example B-7, one part by weight of α-glucosyl rutin, and 40 parts by weight of ethanol. The product can be suitably used as a skin-beautifying agent and skin-whitening agent by diluting 100–10,000 fold in hot water in a bathtub. Similarly as above, the product can be arbitrarily used by diluting in water for face wash or beauty wash before use.

EXAMPLE B-25

Ointment

One part by weight of sodium acetate trihydrate and four parts by weight of calcium DL-lactate were mixed to homogeneity with 10 parts by weight of glycerine, and the mixture was added to a mixture consisting of 50 parts by weight of petrolatum, 10 parts by weight of vegetable wax, five parts by weight of lanoline, 14.5 parts by weight of sesame oil, six parts by weight of a composition containing dokudami obtained by the method in Example B-11, and 0.5 part by weight of peppermint oil. The mixture thus obtained was further mixed to homogeneity into an ointment having an active-oxygen eliminating activity of about 54 units/g product. The product can be arbitrarily used as an antipyic agent, skin-beautifying agent, skin-whitening agent, and agent for promoting the treatment for traumas and burns.

EXAMPLE B-26

Tablet

Twenty parts by weight of ascorbic acid were mixed to homogeneity with 13 parts by weight of crystalline β-maltose, four parts by weight of corn starch, three parts by weight of a composition containing plantain and trehalose obtained by the method in Experiment 5 according to the present invention. The resulting mixture was tabletted into a tablet using a 20R punch, 12 mm in diameter. The tablet had an oxygen eliminating activity of over 560 units/g product, and can be administered orally to subjects 1–10 tablets/adult/day. Especially, it can be used for removing fever and maintaining/controlling stomach and intestinal conditions.

As described above, the present invention provides a reduction inhibitory agent for active-oxygen eliminating activity which comprises trehalose as an effective ingredient, a method for inhibiting the reduction of active-oxygen eliminating activity characterized in that it comprises incorporating either trehalose or the reduction inhibitory agent into products to be treated, and a composition which contains plant an edible substance and/or a plant antioxidant where the reduction of active-oxygen eliminating activity is satisfactorily inhibited by the above method. Intake of the present composition easily supplements to living bodies and enriches living bodies with and functional ingredients such as vitamins, minerals, and edible fibers of plant edible substances. Therefore the present composition contributes greatly to maintain and promote your health, prevent aging and geriatric diseases, promote the treatment of incurable diseases, and inhibit carcinogenesis. Thus the establishment of the present invention would explore a novel health resource as a fourth functional ingredient usable in the fields of processings and applications of plant edible substances, and will give a great contribution to a wide variety of fields, especially, industrial fields of food products, cosmetics, and pharmaceuticals.

While there has been described what is at present considered to be the preferred embodiments of the invention, it will be understood the various modifications may be made therein, and it is intended to cover in the appended claims all such modifications as fall within the true spirits and scope of the invention.

What is claimed is:

1. A method for increasing the residual active-oxygen-eliminating activity of at least one member selected from the group consisting of alpha-glucosyl hesperidin and catechin in an aqueous system containing at least one of alpha glucosyl hesperidin and catechin, comprising incorporating trehalose in said aqueous system.

2. The method according to claim 1 which further comprises a step of sterilizing.

* * * * *